(12) United States Patent
Atmanspacher et al.

(10) Patent No.: US 11,941,756 B2
(45) Date of Patent: Mar. 26, 2024

(54) COMPUTER-IMPLEMENTED METHOD, DETERMINATION SYSTEM, COMPUTER PROGRAM AND ELECTRONICALLY READABLE STORAGE MEDIUM FOR DETERMINING PRODUCTION VALUES FOR PRODUCING A CUSTOM-TAILORED KNITTED GARMENT

(71) Applicant: MEDI GMBH & CO KG, Bayreuth (DE)

(72) Inventors: Jan Atmanspacher, Warmensteinach (DE); Wolfgang Tannebaum, Weiden (DE)

(73) Assignee: MEDI GMBH & CO KG, Bayreuth (DE)

( * ) Notice: Subject to any disclaimer, the term of this patent is extended or adjusted under 35 U.S.C. 154(b) by 511 days.

(21) Appl. No.: 17/196,287

(22) Filed: Mar. 9, 2021

(65) Prior Publication Data
US 2021/0274874 A1    Sep. 9, 2021

(30) Foreign Application Priority Data
Mar. 9, 2020 (EP) .................................... 20161813

(51) Int. Cl.
*G06T 17/10*    (2006.01)

(52) U.S. Cl.
CPC .... *G06T 17/10* (2013.01); *G05B 2219/45194* (2013.01); *G06T 2207/30124* (2013.01)

(58) Field of Classification Search
None
See application file for complete search history.

(56) References Cited

U.S. PATENT DOCUMENTS

| 4,502,301 A | * | 3/1985 | Swallow | A61F 13/08 66/178 A |
| 4,768,357 A | * | 9/1988 | Ohtake | D04B 1/104 66/126 R |
| 5,442,564 A | * | 8/1995 | Merlini | D04B 9/025 66/54 |

(Continued)

FOREIGN PATENT DOCUMENTS

| EP | 1756343 A1 | 2/2007 | |
| GB | 2602094 A * | 6/2022 | ............. A41H 3/007 |
| WO | 2005106087 A1 | 11/2005 | |

*Primary Examiner* — Grace Huang
(74) *Attorney, Agent, or Firm* — Rimon PC

(57) ABSTRACT

This invention discloses a computer-implemented method for determining production values for producing a custom-tailored knitted garment for a limb of a person. A 3D scan device acquires a three-dimensional data of a limb. A height value describing the dimension of a knitting row in the lengthwise direction of the limb and a total length value for at least one lengthwise section of the garment are provided, and the number of knitting rows for one section of the garment is determined by dividing the total length value by the height value. A circumference information describing the circumference of the limb is derived by evaluating the three-dimensional dataset. A circumference value for each n-th knitting row or each knitting row except every n-th knitting row is determined from the circumference information. The circumference value is used for determining production values for the knitted garment.

15 Claims, 3 Drawing Sheets

(56) References Cited

U.S. PATENT DOCUMENTS

| | | | | |
|---|---|---|---|---|
| 5,511,394 | A * | 4/1996 | Shima | D04B 1/126 66/54 |
| 7,043,329 | B2 * | 5/2006 | Dias | D04B 15/50 66/55 |
| 10,842,680 | B1 * | 11/2020 | Weiler | G16H 20/00 |
| 10,900,152 | B2 * | 1/2021 | Sasaki | D04B 1/22 |
| 2012/0035510 | A1 * | 2/2012 | Cros | D04B 1/265 600/592 |
| 2020/0008502 | A1 | 1/2020 | Deguzman et al. | |
| 2020/0249657 | A1 * | 8/2020 | Schaumber | D04B 1/26 |
| 2020/0375270 | A1 * | 12/2020 | Holschuh | B32B 5/08 |
| 2022/0167874 | A1 * | 6/2022 | Job | A61B 5/1072 |

* cited by examiner

COMPUTER-IMPLEMENTED METHOD, DETERMINATION SYSTEM, COMPUTER PROGRAM AND ELECTRONICALLY READABLE STORAGE MEDIUM FOR DETERMINING PRODUCTION VALUES FOR PRODUCING A CUSTOM-TAILORED KNITTED GARMENT

CROSS-REFERENCE TO RELATED APPLICATIONS

This application claims priority to European Patent Application serial no. 20 161 813.9 filed Mar. 9, 2020, the contents of which is incorporated herein by reference in its entirety as if set forth verbatim.

DESCRIPTION

Computer-implemented method, determination system, computer program and electronically readable storage medium for determining production values for producing a custom-tailored knitted garment

BACKGROUND OF THE INVENTION

The invention concerns a computer-implemented method for determining production values for producing a custom-tailored, in particular skin-tight, knitted garment for a limb of a person, wherein a three-dimensional dataset of the limb acquired using a 3D scan device is received. The invention further concerns a determination system, a computer program and an electronically readable storage medium.

Knitted garments for a limb of a person, in particular for use in medical and/or sports applications, are often custom-tailored for perfect fit regarding not only optics, but also desired medical and/or supporting effects. Such a compression garment may, for example, be a stocking for an arm or a leg, a wrap, or an orthosis, and may in particular be a compression garment.

To produce a custom-tailored, in particular skin-tight, knitted garment for a limb of a person, certain production values describing the shape and the dimensions of the limb are required. For example, for compression garments, standards have been developed defining certain measurement positions, at which, in the case of compression garments, usually also compression is measured. An example for such a standard is RAL-GZ 387/1 in Germany.

Hence, the traditional way to obtain production values is to have staff measure at the limb, for example circumferences, at estimated measurement positions corresponding to the measurement positions provided by the standard. To obtain more precise production values, in particular circumference values, it has been proposed to scan the limb using a 3D scan device, which may be a dedicated 3D scanner, but also an especially configured handheld mobile device, for example a smartphone, acquiring multiple views of the limb from different angles to calculate a 3D model of the limb. In any case a three-dimensional dataset of the limb, in particular its surface, results.

In such a three-dimensional dataset of the surface of the limb, the measurement positions provided by the respective standard may be recognized and marked manually, such that the circumference values at the manually marked measurement positions may be derived from the three-dimensional dataset.

In not yet laid-open European patent application EP 19167008.2, a computer-implemented method for automatically deriving measurement positions according to a standard in a three-dimensional dataset was proposed, wherein the reference position of an anatomical feature of the limb along the length of the limb is determined in the dataset and the at least one measurement position is determined from this reference position by using at least one rule of a rule set, wherein each rule relates at least one reference information to at least one measurement position.

BRIEF SUMMARY OF THE INVENTION

Once circumference values of the limb at these measurement points are known, they may be converted into production values, possibly compression values, and the custom-tailored knitted garment may be produced.

In these methods according to the state of the art, information may be lost, since a complete three-dimensional dataset of the limb is reduced to a small number of circumference values at predefined measurement positions, which may or may not correspond to actual knitting rows.

It is an object of the current invention to provide a method resulting in the production of improved custom-tailored knitted garments.

This object is achieved by providing a computer-implemented method, a determination system, a computer program and an electronically readable storage medium according to the independent claims. Advantageous embodiments are described in the dependent claims.

A computer-implemented method for determining production values for producing custom-tailored, in particular skin-tight, knitted garment for a limb of a person comprises the steps of
  receiving a three-dimensional dataset of the limb acquired using a 3D scan device,
  receiving at least one height value describing the dimension of a knitting row in the length direction of the limb and at least one total length value for at least one lengthwise section of the garment and
  determining a number of knitting rows for the at least one section of the garment by dividing the total length value by the height value,
  evaluating the three-dimensional dataset to derive a circumference information describing the circumference of the limb along at least the length of the limb covered by the at least one section,
  from the circumference information, determining a circumference value for each n-th knitting row or each knitting row except every n-th knitting row, wherein n is a natural number, in the at least one section,
  wherein the circumference values are used as and/or for deriving production values for the knitted garment.

The invention allows the completely automatic determination of production values for a custom-tailored knitted garment by using and evaluating a three-dimensional dataset of the limb of the person. 3D scan devices able to scan limbs, in particular a leg of a person, have already been proposed in the state of the art and may, for example, use imaging techniques. The resulting three-dimensional dataset should at least describe the surface of the limb, that is, its outline, but can also provide additional relevant information. The three-dimensional dataset may be acquired by a contact-free measurement, such that physical contact may be omitted. Preferably, the three-dimensional dataset may be acquired using a contact-free, imaging-based 3D scan device, in particular a tablet or mobile phone running a scanning application.

Regarding the inventive method for determining production values, the section may also comprise the whole garment, such that the total length value for such a lengthwise section of the garment is the total length of the whole garment. This is, in particular, expedient if the knitted garment is a wrap, bandage or otherwise locally applied, for example to an elongate portion of the limb. It is, however, also conceivable to use multiple sections, in particular divide the knitted garment to be used into multiple sections. For example, in case of a stocking, sections may be defined for the foot and the leg. It is, in particular, possible to assign different values of n to different sections, such that, for example, in one section, a circumference value is determined for each knitting row (n=1), while in another section, circumference values may only be determined for each second or third knitting row (n=2 or 3).

The invention thus proposes not to reduce the information found in a three-dimensional dataset of the limb to only a few circumference values at measurement positions defined, for example, by a standard, but to use larger amounts of the information in a manner that is specifically designed and developed with regard to the knitting process. In particular, the circumference values are determined at measurement positions associated with knitting rows that will later be actually knitted. In this regard, a total length value, which is usually predetermined regarding the purpose and/or type of the knitted garment, but may also be, at least partly, derived from the three-dimensional dataset, is used as well as the already known height of the knitting rows, such that the number of knitting rows in a section as well as their position or the intervals, which they span, respectively, may be determined. In summary, the circumference values are purposefully determined in a manner that they are unambiguously associated with a knitting row to be knitted when the knitted garment is produced. This, as a further advantage of the current invention, simplifies and improves the ensuing production process, in particular simplifying the determination of control parameters for a knitting device/machine or the like.

In preferred embodiments, n may be an even number. As can be shown, this allows easier estimation, for example interpolation, where necessary, when determining actual production values for knitting rows for which a circumference value has not been determined from the circumference information.

The value of n is, in the case of determining a circumference value for every n-th knitting row, preferably smaller than or equal twenty, in particular smaller than ten, to provide sufficient data, in particular additional data as compared with predefined measurement positions of a standard. In preferred embodiments, the value of n may be determined dependent on a degree of fitting desired, for example, n=1 could relate to a 100% fit. For a 90% fit, for example, multiple sections may be defined in which n is one or two, respectively. However, it is noted that, as an alternative to determining a circumference value to each n-th row, it is, in particular, also conceivable to leave out each n-th row to achieve a high degree of sampling while yet reducing the number of sampling positions in a controlled manner. In this case, n may, of course, not be equal to one.

Preferably, the knitted garment may be a compression garment, however, the invention may also be applied to other types of garments, in particular skin-tight garments, for which a perfect fit can be achieved by using further information from the three-dimensional dataset. The garment may, in particular, be a stocking, a bandage, a wrap, an orthosis, or other such garments, preferably for medical or sports applications.

In particular in the case that circumference values are determined for each knitting row, up to 100% fitting can be achieved.

In the case where the circumference information comprises multiple scan values for the circumference in each height value interval corresponding to a knitting row along the length direction (longitudinal direction) of the limb, preferably, the circumference value for a knitting row is determined from the multiple scan values in the corresponding height value interval by statistical evaluation, in particular as a mean or maximum or minimum of the scan values. In particular, a mean value has proven to be suitable for deriving a circumference value, from which corresponding production values may be derived.

In particular, the number of stitches and/or stitch width and/or at least one weft property, in particular a weft pretension and/or a weft amount for each knitting row, is determined from the circumference values as further production values. It is, in particular, noted that the current invention can be applied to flat knitting as well as circular knitting, wherein circular knitting may be preferred in some cases. That is, in some applications, the invention may preferably concern a method for determining production values for producing a custom-tailored, circular knitted garment.

However, it has been noticed in the course of developing the invention, in particular, if a circumference value for each knitting row is determined, the resulting 100% fitting may lead to problems regarding the optical impression of the knitted garment, in particular a deviation from the expected optical impression of the person. For example, certain anatomical features may lead to bulges/indentations and the like if each circumference value is taken into account.

This, in turn, may lead to complaints by persons, although the garment they received is, in principle, perfectly fitting. Such problems may also occur if strongly localized measurement or evaluation errors occur, for example outliers.

Consequently, the current invention proposes, in especially preferred embodiments, measures, in particular steps, to improve the optical impression of the produced knitted garment without strongly compromising the fit.

Thus, in an advantageous embodiment, a smoothing filter may be applied to the circumference information and/or the circumference values in the lengthwise direction. The smoothing filter is, for example, useful in removing single outliers and/or strong bends in the course of the circumference information/circumference values in the lengthwise direction. Thus, applying a smoothing filter may already reduce larger gradients in circumference, which may lead to negative visual effects.

In an especially preferred embodiment, at least one optics adaptation criterion may be applied to at least a part of the circumference values and/or values derived therefrom in the lengthwise direction, wherein, if at least one of the at least one optics adaptation criterion is fulfilled, at least one circumference value and/or derived value is adapted and/or at least one new production value is chosen according to a rule associated with the fulfilled optics adaptation criterion. That is, typical optical effects which may lead to complaints or generally, unwanted optical impressions, may be described by certain optics adaptation criteria, such that the optical impression of the knitted garments can be automatically improved and optimized, in particular guided by rules, which may have been determined empirically and/or based on respective knowledge.

Preferably, at least one of the at least one optics adaptation criterion evaluates an, in particular local, slope of the circumference values and/or derived values, in particular by comparing with at least one threshold value, and/or a local shape resulting from the circumference values and/or derived values, in particular regarding the presence of local indentations, and/or compares the circumference values with at least one comparison curve. That is, preferably, a sort of optics slope (gradient) check may be performed by at least one of the at least one optics adaptation criterion. If the, in particular local, slope is analyzed, it can be shown that features of the knitted garment leading to undesired visual effects can be robustly detected and identified. However, in particular additionally, it may be advantageous to also analyze a local shape, for example regarding the presence of local indentations or bulges. Finally, a comparison curve may be provided defining an optimal shape of the specific knitted garment to be produced regarding optics, such that deviations can be detected and, at least partially, corrected.

Knitting provides several possibilities to adjust the knitting scheme to provide a better optical impression and/or to further improve fitting. In preferred embodiments, the further production values may describe the amount of weft and/or the pretension of at least one thread and/or a stitch number and/or a stitch size and/or the presence of at least one partial knitted row. Preferably, for flat knitting, the amount of weft thread and/or the increase or decrease of stitches may be relevant production parameters, while, regarding circular knitting, the pretension, the presence of at least partial knitted row and/or the stitch size are preferred production parameters to adjust optics and/or fitting. In particular, for example, partial knitted rows may be used to mitigate large slopes and/or to even increase slopes which are too low. Regarding the pretension of the weft, the circumference value may be kept as determined from the circumference information, however, compression may be increased in the respective knitting row.

In principle, it is also conceivable in the current invention to use at least one artificial intelligence optics adaptation algorithm, which may implement at least one optics adaptation criterion. In particular, at least one artificial intelligence optics adaptation algorithm may be applied to at least a part of the circumference values and/or values derived thereof in the lengthwise direction for adapting at least one production value regarding the optical impression of the garment.

In especially preferred embodiments, at least one optics adaptation criterion has been defined and/or the optics adaptation algorithm has been trained based on complaint data regarding returned garments. As already explained, undesired optical impressions often lead to complaints despite the garment itself being of an at least near-perfect fit. Thus, such complaints may be used as a basis for defining the optics adaptation criteria or, when using machine learning, to train the optics adaptation algorithm, preferably implementing at least one optics adaptation criterion. For example, production values and/or circumference values regarding knitted garments that had no complaints as well as garments that had complaints, including the complaint status, may be used as training data and/or basic data for formulating optics adaptation criteria, for example by statistical evaluation.

In summary, knitted garments may not only be produced to better fits, but also be designed to fulfill a certain optical impression norm, such that the number of complaints may be reduced and an optically appealing knitted garment may be produced.

However, in some applications, circumference values associated with measurement positions predefined by a standard, may, in particular additionally, be required or useful. Thus, in embodiments of the current invention, the positions of the circumference values may be chosen to encompass at least one measurement position defined by a standard, in particular RAL. For example, n may be chosen such that at least some measurement positions defined by a standard are met at least essentially. However, since the position of knitting rows and measurement positions defined by a standard may not in any case sufficiently accurately match, preferably, at least one additional circumference value may be determined at at least one additional measurement position defined by a standard, in particular RAL. In preferred embodiments, the at least one additional measurement position may be determined by deriving a reference position of an anatomical feature of the limb along the length of the limb from the dataset, and determining the additional measurement position using at least one rule of a rule set, wherein each rule relates at least one reference position to at least one additional measurement position.

Such an approach has been proposed in the already-mentioned, not yet laid-open European patent application EP 19167008.2. It can also advantageously be applied here, since the additional measurement positions and the additional circumference values may be fully automatically determined based on the three-dimensional dataset of the limb. In this manner, two sets of circumference values result, one for every n-th knitting row and one according to measurement positions of a standard, determined on the basis of a rule set. Both may be used to provide production values leading to an optimized knitted garment for a respective purpose. For example, the additional circumference values may be taken into account to adapt certain production parameters/production values, in particular as discussed above regarding optics adaptation, to assure providing a certain effect of the knitted garment at the additional measurement positions. This may, for example, comprise adapting pretension in knitting rows adjacent to a measurement position of a standard, adding partial knitting rows, adapting the amount of weft threads and/or a stitch number and/or a stitch size and the like. In summary, the detailed circumference information in the three-dimensional dataset is optimally exploited regarding optimized fitting of the garment and optimized achievement of desired effects related to measurement positions defined by a standard.

As already indicated, the knitted garment may, in particular, be a compression garment. Regarding such a compression garment, a preferred, advantageous embodiment provides that at least one tension value is calculated from each circumference value as a skin value. The skin value usually describes the circumference of the limb without any applied compression and is thus equivalent to the circumference value. The tension value describes the circumference of the limb with the compression garment applying a desired compression. Usually, the tension value is measured manually, leading to shortcomings and a large dependency on the proficiency of the staff performing the measurement. However, as has been shown, to determine the tension value, which is being used along with the circumference value (skin value) for the production of the custom-tailored compression garment, the tension value of the limb may be calculated from the skin value according to a calculation instruction parametrized by at least one parameter, the parameter being derived from a dataset comprising multiple associated tuples of skin values and tension values. For example, the parameter may be a factor with which the skin value of the limb is multiplied. Such an approach has, for example, being proposed in not yet late-open European patent application EP 19155558.0 and can also be implemented in the method according to the invention to provide full automatization and a high robustness and precision.

The invention also concerns a method for producing a custom-tailored knitted garment for a limb of a person, comprising automatically performing the steps of a method according to the invention for determining production values, whereafter the knitted garment is automatically produced by a garment production apparatus, in particular a knitting machine, using the determined production values. In particular, a computing device of a manufacturer may receive, in particular along with further information, the three-dimensional dataset and/or the production values, the three-dimensional dataset being, for example, measured in a medical store. Automatically, the production values are determined. At this time, all information for automatically producing the custom-tailored knitted garment for the limb of the person is available at the computing device of the manufacturer, such that the garment production apparatus, in particular a knitting machine, can be controlled to correspondingly produce the custom-tailored knitted garment for the limb of the person. Thus, a fully automatic, reliable and simply implementable way of producing custom-tailored compression garments is provided.

The invention further concerns a determination system for determining production values for producing a custom-tailored, in particular skin-tight, knitted garment for a limb of a person, comprising
- a first interface for receiving a three-dimensional dataset of the limb acquired using a 3-D scan device,
- a second interface for receiving at least one height value describing the dimension of a knitting row in the lengthwise direction of the limb and at least one total length value for at least one lengthwise section of the garment,
- a first determination unit for determining a number of knitting rows for the at least one section of the garment by dividing the total length value by the height value,
- an evaluation unit for evaluating the three-dimensional dataset to derive a circumference information describing the circumference of the limb along at least the length of the limb covered by the at least one section,
- a second determination unit for determining, from the circumference information, a circumference value for each n-th knitting row or each knitting row except every n-th knitting row, wherein n is a natural number, in the at least one section,
- a third interface for providing the circumference values and/or production values derived therefrom.

In other words, the determination system is configured to perform a determination method according to the invention. All features and remarks relating to the determination method accordingly apply to the determination system according to the invention.

A computer program according to the invention performs the steps of a method according to the invention when the computer program is executed on a computing device, in particular of a determination system and/or as described, a computing device of a manufacturer. The computer program may be stored on an electronically readable storage medium according to the invention, which thus comprises control information comprising at least one computer program according to the invention, such that, when the storage medium is used in a computing device, the computing device executes the steps of a method according to the invention.

BRIEF DESCRIPTION OF THE DRAWINGS

Further details and advantages of the current invention become apparent from the following description of detailed embodiments, taken in conjunction with the drawings, in which.

DETAILED DESCRIPTION OF THE INVENTION

Figure 1:
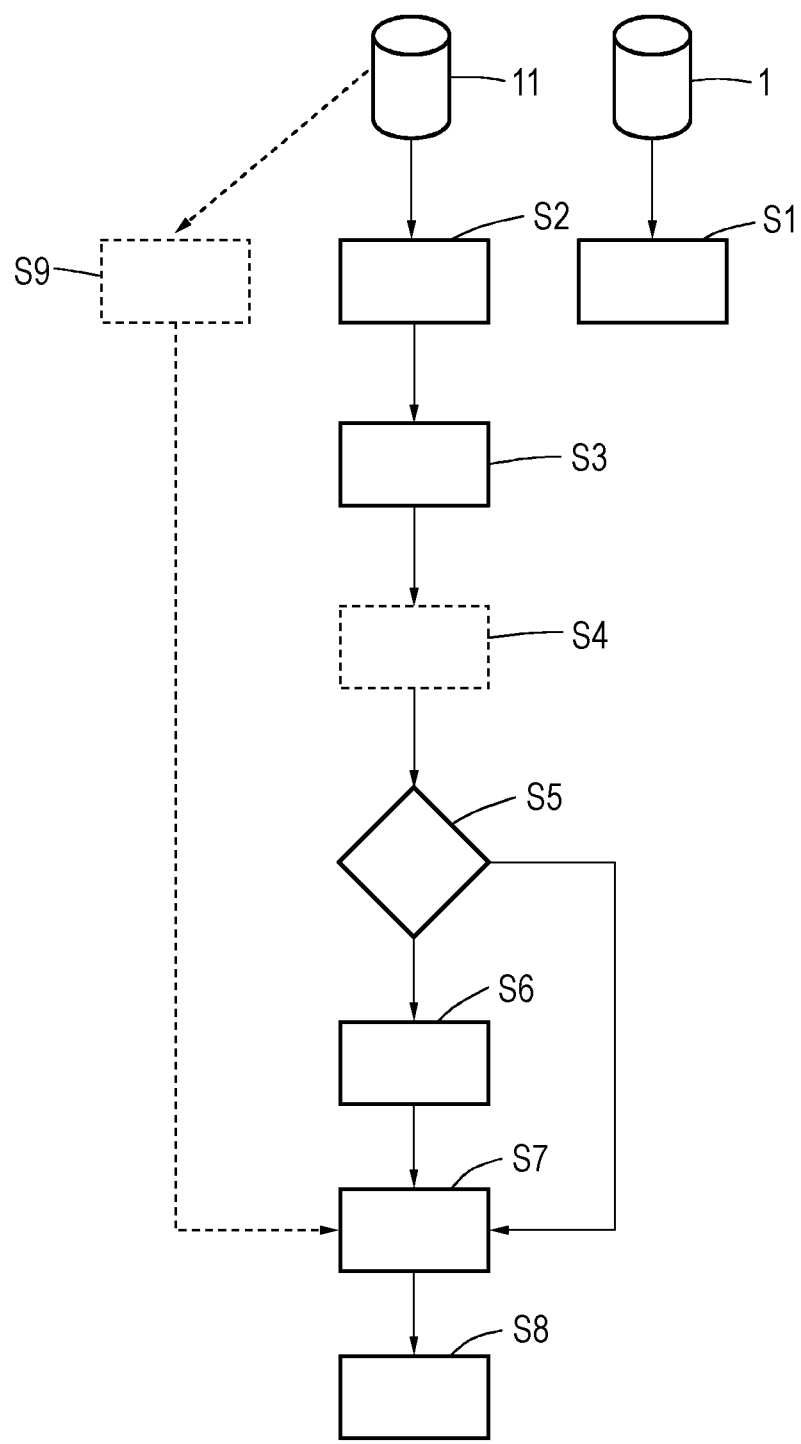
FIG. 1 is a flowchart of an embodiment of a method according to the invention.

FIG. 1 is a flowchart of an example embodiment of a method according to the invention. In the computer-implemented method shown, production values for producing a custom-tailored knitted garment, in this case a compression garment, for a limb, in this case a leg, of a person are determined and, optionally, also automatically used to produce the knitted garment based on the determined production values.

In a step S1, at least one height value describing the dimension of a knitting row in a length direction of the limb and at least one total length value for at least one lengthwise section of the garment are received and the number of knitting rows for the at least one section of the garment is determined by dividing the total length value by the height value. The input parameters 1, that is, the height value and the total length value, are also indicated in FIG. 1. They may, for example, be received as a presetting, however, it is also possible to use actual information about the length of the limb of the person, in particular from a three-dimensional dataset as discussed below, in conjunction with a general size requirement of the garment to calculate the length of the at least one section, which may, in embodiments, also comprise the whole knitted garment.

Figure 2:
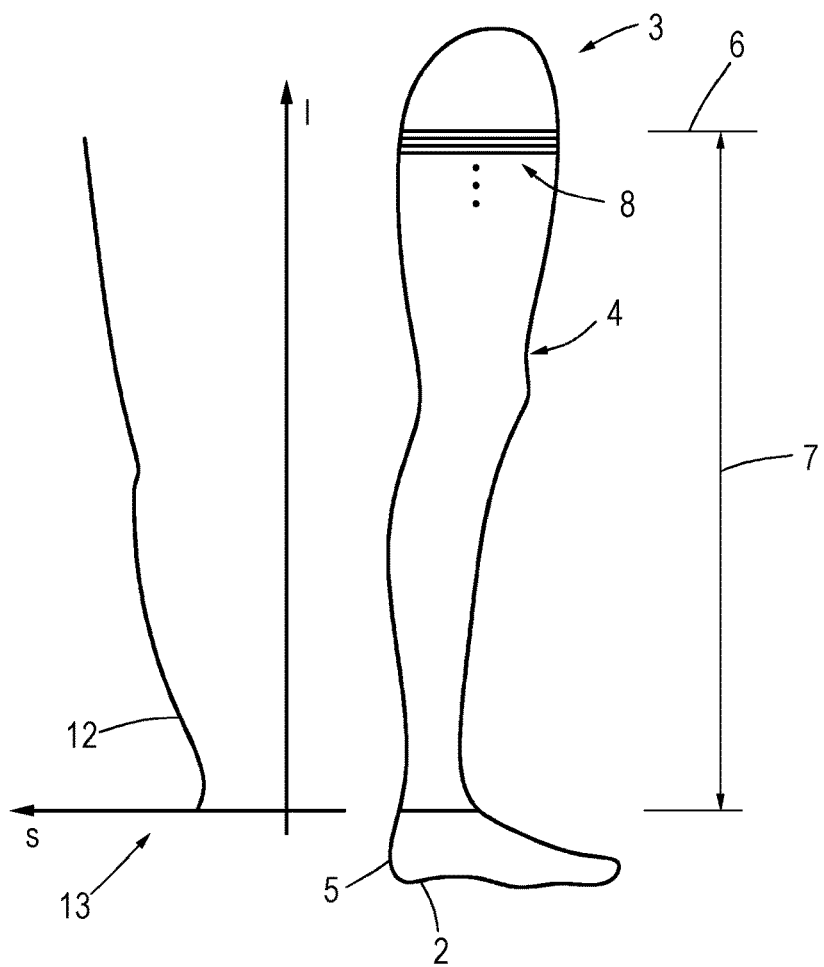
FIG. 2 shows a schematic depiction of a leg and corresponding circumferences.

In FIG. 2, a principle sketch of a leg 2 as the limb 3 is shown. The exemplary section 4 extends from the ankle 5 to a position 6 on the thigh. The section 4 spans a total length 7 also indicated in FIG. 2.

If, now, the height of a knitting row 8 is known, the length 7 can be filled with these knitting rows such that each knitting row spans a height value interval along the lengthwise direction of the limb 3, as indicated by the lines 8 and the ellipsis indicated in the thigh area. In this manner, the number of knitting rows in the section 4 as well as the position and extension are known.

Figure 3:
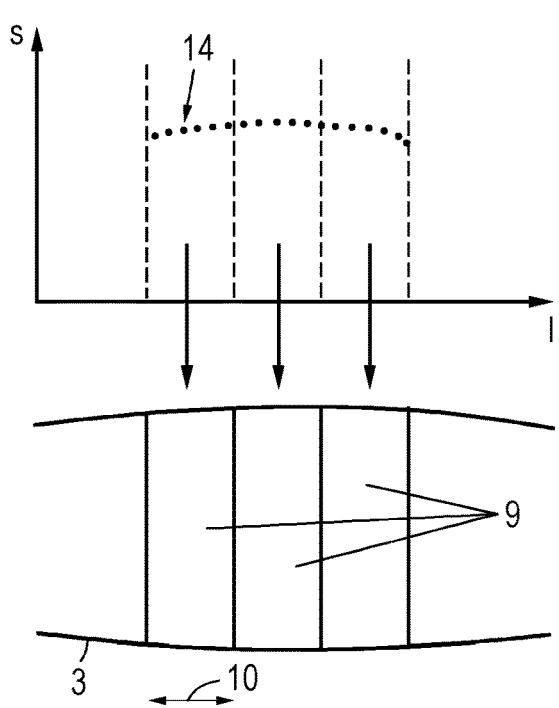
FIG. 3 shows a detail of a limb and corresponding circumferences.

This is, in more detail, shown in FIG. 3, shown for only a small part of the limb 3. Three knitting rows 9 are indicated, each spanning a height value interval 10 in the lengthwise direction of the limb 3.

Returning now to FIG. 1, in a step S2, if not already used for determining the total length, a three-dimensional dataset 11 of the limb 3, which was acquired by a 3D scanning device, in particular a mobile device like a tablet or a mobile phone running a corresponding application, is received. Also in step S2, the three-dimensional dataset 11 is evaluated to derive a circumference information describing the circumference of the limb 3 along at least the length of the limb 3 covered by the section 4. Such a circumference information is depicted in FIG. 2 as a curve 12 in the graph 13, wherein the ordinate shows the scan value s for the circumference, the abscissa the length I along the limb 3. This evaluation is possible since the three-dimensional dataset 11 describes the surface of the limb 3.

In a step S3, the circumference information is used to determine a circumference value for, in this case each, knitting row 9 in the section 4. Alternatively or for other sections 4, it is also possible to determine the circumference value only for each n-th knitting row, where n>1, for example for each second or third knitting row 9. Further, it is conceivable to determine the circumference value for every knitting row except every n-th knitting row, wherein n>2 in this case, to implement a high, but yet not complete sampling.

As shown in FIG. 3, in each height value interval, multiple scan values 14 for the circumference are comprised by the circumference information due to high spatial resolution. To determine the circumference value, these scan values 14 for each height value interval 10 are statistically evaluated, in particular by calculating a mean value as the circumference value. Alternatively, a maximum or a minimum may also be used.

Returning now to FIG. 1, in an optional step S4, a smoothing filter may be applied to the circumference information and/or the circumference value in the lengthwise direction. Additionally or alternatively, an outlier detection may be performed to detect or remove outliers. Of course, if the smoothing filter and/or the outlier detection are to be applied to the circumference information, step S4 takes place before step S3. In any case, a curve representing the circumference value is smoothed and/or undesired outliers, for example due to evaluation or measurement errors, may be removed.

In a step S5, multiple optics adaptation criteria are applied to the circumference values. The optics adaptation criteria check whether undesired optical effects might be present in the produced knitted garment if those circumference values are used, in particular without adapting further production values. For example, a first optics adaptation criterion checks whether a, in particular local slope (gradient) of the circumference values and/or values derived therefrom exceeds at least one threshold, such that sudden changes in gradient may be detected. A second optics adaptation criterion evaluates a local shape, in particular regarding the presence of local indentations and/or bulges. This is exemplarily indicated in FIG. 4, where the curve 15 illustrates the outline according to circumference values determined in step S3 in an example. As can clearly be seen, an indentation 16 is present, which would compromise the optical impression of the garment when produced.

In a third optics adaptation criterion in step S5, the circumference values, in particular their curve 15, is compared with at least one comparison curve and the deviation is compared with another threshold value.

If any of the optics adaptation criteria in step S5 is fulfilled in a step S6, action is taken to adapt the at least one circumference value and/or a derived value and/or to choose at least one new production value such that the optical flaw is removed, in particular without noticeably compromising a medical or sports effect to be exerted by the knitted garment, in particular compression garment, and without noticeably compromising the all-over-fit.

Figure 4:
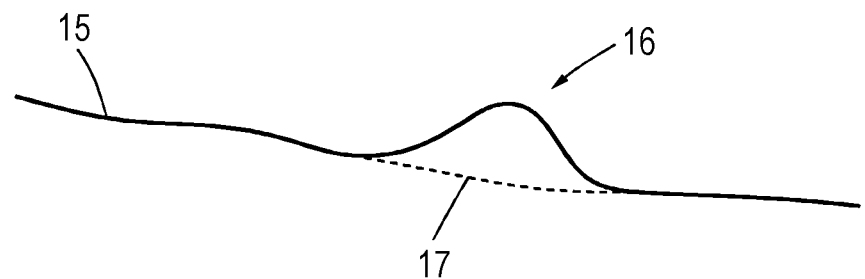
FIG. 4 is an illustration regarding an indentation in a garment.

Depending on the optical flaw detected, multiple possibilities to adapt circumference values and/or further production values are possible. For example, as shown in FIG. 4 by the dashed curve 17, the circumference values may be adjusted to provide a smoother corrected curve 15, 17, 15. However, it is also possible to adapt the amount of weft threads and/or the pretension of the weft thread and/or stitch number and/or stitch size and/or the presence of at least one partial knitted row. The usage of the partial knitted rows is in particular advantageous if high slopes are to be mitigated and the like. In the case of FIG. 4, for example, alternatively the pretension in areas around the possible indentations 16 may be increased such that the knitted garment, when not worn, automatically flattens out the indentation 16. Of course, other ways to adapt also exist depending on the limb, the anatomical area, the type of optical flaw and/or other factors.

If none of the optics adaptation criteria in step S5 is fulfilled, and as soon as circumference values and/or further production values are adapted in step S6, the method proceeds to step S7. In step S7, the final set of production parameters is determined and/or compiled. Production parameters, of course also comprising the already named further production values, may comprise a number of stitches and/or stitch width and/or at least one weft property for each knitting row, taking into account possible adaptations performed in step S6. In the case of a compression garment, for each circumference value, which is then understood as a skin value, a tension value may also be determined, as laid out above in the general description.

An optional step S9 may also be performed if, additionally to the circumference values determined in step S3 (and potentially adapted in step S6), additional circumference values are to be determined at additional measurement positions defined by a standard, in particular RAL. In step S9, the three-dimensional dataset 11 may also be evaluated to first derive a reference position of an anatomical feature of the limb along the length of the limb from the dataset 11, and afterwards determine the additional measurement position using at least one rule of a rule set, wherein each rule relates at least one reference position to at least one additional measurement position. In this manner, two sets of circumference values exist: one, determined in the steps S1-S6, in a high resolution, in particular for each knitting row, and another, determined in step S9, for certain predefined measurement positions of a standard, which may not exactly coincide with positions of the knitting rows. However, for further optimizing the fit of the knitted garment and its desired effect, these additional circumference values may also be taken into account when determining final production parameters in step S7.

If the production of the knitted garment shall also be performed fully automated, the step S8, the production values, may be used to control a garment production apparatus, in particular a knitting machine, to produce the knitted garment.

It should be noted that at least one of the optics adaptation criteria may also be implemented by at least one artificial intelligence optics adaptation algorithm, which may also combine steps S5 and S6. Generally, the optics adaptation criteria have preferably been defined based on complaint data regarding returned garments. In the case of the optics adaptation algorithm, the complaint data may form part of a training data used in machine learning for the artificial intelligence optics adaptation algorithm.

Figure 5:
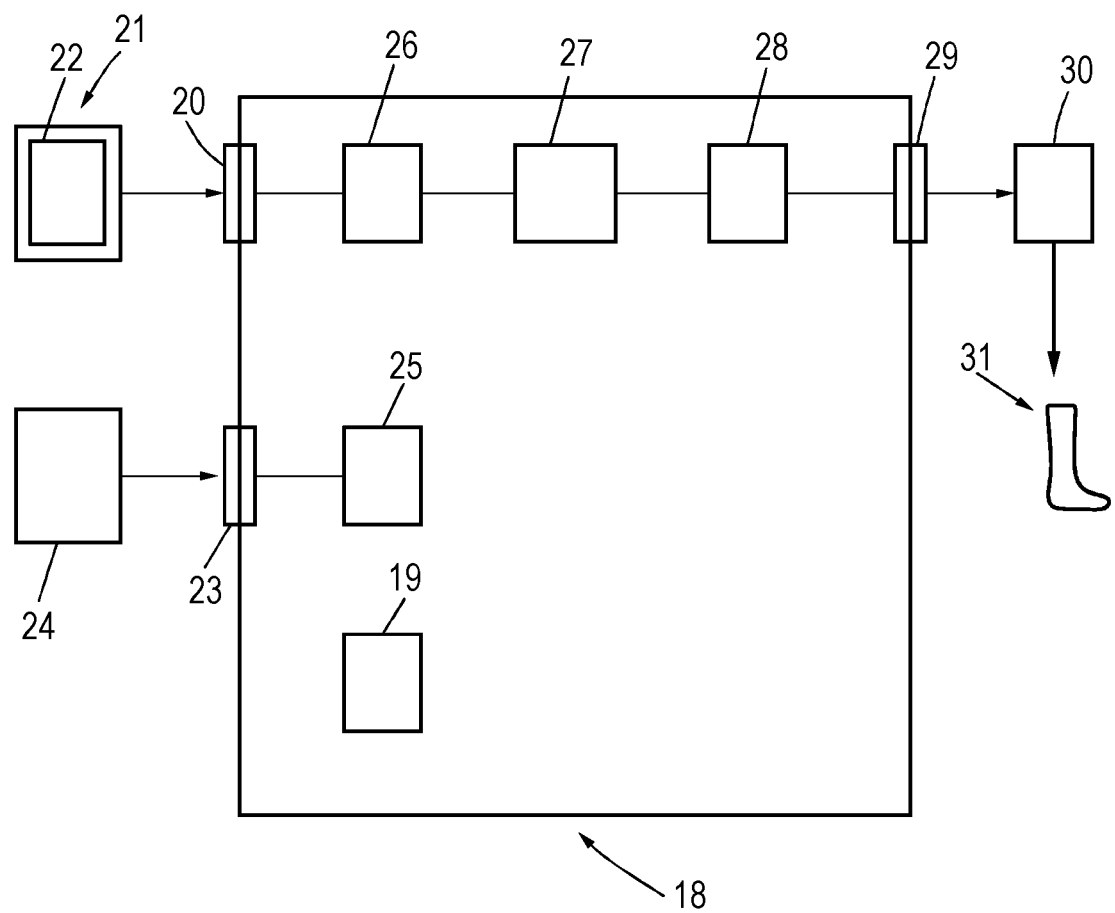
FIG. 5 shows a determination system according to the invention.

FIG. 5 finally shows a principle drawing of a determination system 18 according to the current invention. The determination system 18 may comprise at least one computing device, in particular a computing device of a manufacturer, which, in turn, usually has at least one processor (not shown) and at least one storage means 19. Functional units to be discussed with respect to FIG. 5 as well as further functional units may be implemented as hardware and/or software, in particular using the at least one processor.

The determination system 18 comprises a first interface 20 for receiving the three-dimensional dataset 11 of the limb 3, in particular from the used 3D scanning device 21, which may, as discussed, for example be a mobile phone 22 having a camera and running a corresponding application.

Via a second interface 23, information regarding the total length value and the height value may be received, in particular from another or the same computing device 24, which may or may not be identical to the 3D scanning device 21.

In a first determination unit 25, the number of knitting rows 9 for the section 4 is determined according to step S1. In an evaluation unit 26, the three-dimensional dataset 11 is evaluated according to step S2. In a second determination unit 27 the circumference values according to step S3 are determined, while, in an optics adaptation unit 28, the steps S5 and S6 may be performed. The final set of production values is compiled and output by a third interface 29, step S7, for example to a knitting machine 30. The knitting machine 30 may produce the custom-tailored compression garment 31 according to these production values.

Of course, the determination system 18 may comprise further functional units, in particular regarding optional steps as discussed regarding FIG. 1.

The invention claimed is:

1. Computer-implemented method for producing a custom-tailored, skin-tight, knitted garment (31) for a limb (3) of a person, comprising the steps of:
   receiving a three-dimensional dataset (11) of the limb (3) acquired using a 3D scan device (21),
   receiving a height value describing the dimension of a knitting row (9) in the lengthwise direction of the limb (3) and a total length value for at least one lengthwise section (4) of the garment (31) and determining a number of knitting rows (9) for the at least one section (4) of the garment (31) by dividing the total length value by the height value,
   evaluating the three-dimensional dataset (11) to derive a circumference information describing the circumference of the limb (3) along at least the length of the limb (3) covered by the at least one section (4),
   from the circumference information, determining a circumference value for each n-th knitting row (9) or each knitting row (9) except every n-th knitting row (9), wherein n is a natural number, in the at least one section (4),
   wherein the circumference values are used for determining production values for the knitted garment (31).

2. The method according to claim 1, characterised in that the circumference information comprises multiple scan values (14) for the circumference in each height value interval (10) corresponding to each knitting row (9) along the lengthwise direction, wherein each circumference value for each knitting row (9) is determined from the multiple scan values (14) in the corresponding height value interval by statistical evaluation as a mean or a maximum or a minimum of the scan values (14).

3. The method according to claim 1, characterised in that a number of stitches and/or a stitch width and/or at least one weft property and/or a weft pretension and/or a weft amount for each knitting row (9) is determined from the circumference values as the production values.

4. The method according to claim 1, characterised in that a smoothing filter is applied to the circumference information and/or the circumference values in the lengthwise direction.

5. The method according to claim 1, characterized in that at least one optics adaptation criterion is applied to at least a part of the circumference values and/or values derived therefrom in the lengthwise direction, wherein, if at least one of the at least one optics adaptation criterion is fulfilled, at least one circumference value and/or derived value is adapted and/or at least one new production value is chosen according to a rule associated with the fulfilled optics adaptation criterion.

6. The method according to claim 5, characterised in that at least one of the at least one optics adaptation criterion evaluates a local slope of the circumference values and/or the derived values by comparing with at least one threshold value, and/or a local shape resulting from the circumference values and/or the derived values regarding the presence of local indentations (16), and/or compares the circumference values with at least one comparison curve.

7. The method according to claim 5, characterised in that the at least one new production value describes the amount of weft threads and/or the pretension of at least one thread and/or a stitch number and/or a stitch size and/or the presence of at least one partial knitted row (9).

8. The method according to claim 1, characterised in that at least one artificial intelligence optics adaptation algorithm is applied to at least a part of the circumference values and/or values derived thereof in the lengthwise direction for adapting at least one production value regarding the optical impression of the garment (31).

9. The method according to claim 8, characterised in that at least one optics adaptation criterion has been defined and/or the at least one optics adaptation algorithm has been trained based on complaint data regarding returned garments.

10. The method according to claim 1, characterised in that the positions of the circumference values are chosen to encompass at least one measurement position defined by the standard RAL-GZ 387/1, and/or at least one additional circumference value is determined at at least one additional measurement position defined by each standard RAL-GZ 387/1.

11. The method according to claim 1, characterised in that the garment (31) is a compression garment (31), wherein a tension value is calculated from each circumference value as a skin value.

12. Method comprising the steps of: automatically performing the steps of the method according to claim 1, whereafter automatically producing the knitted garment (31) by a garment production apparatus using the determined production values.

13. Computer program, which performs the steps of the method according to claim 1 when the computer program is executed on a computing device within a determination system (18).

14. Electronically readable storage medium, on which the computer program according to claim 13 is stored.

15. Determination system (18) for producing a custom-tailored, skin-tight, knitted garment (31) for a limb (3) of a person, comprising:
- a first interface (20) for receiving a three-dimensional dataset (11) of the limb (3) acquired using a 3D scan device (21),
- a second interface (23) for receiving a height value describing the dimension of a knitting row (9) in the lengthwise direction of the limb (3) and a total length value for at least one lengthwise section (4) of the garment (31),
- a first determination unit (25) for determining a number of knitting rows (9) for the at least one section (4) of the garment (31) by dividing the total length value by the height value,
- an evaluation unit (26) for evaluating the three-dimensional dataset (11) to derive a circumference information describing the circumference of the limb (3) along at least the length of the limb (3) covered by the at least one section (4),
- a second determination unit (27) for determining, from the circumference information, a circumference value for each n-th knitting row (9) or each knitting row (9) except every n-th knitting row (9), wherein n is a natural number, in the at least one section (4),
- a third interface (29) for providing the circumference values and/or for production values derived therefrom.

\* \* \* \* \*